United States Patent
Pai et al.

(10) Patent No.: US 6,337,631 B1
(45) Date of Patent: Jan. 8, 2002

(54) AUTOMATIC INFUSION-MONITORING INSTRUMENT

(76) Inventors: Min-Fang Pai, 6Fl., No. 16, Lane 79, Sec. 2, Jianguo S. Rd., Daan Chiu, Taipei 106; Yu-Yueh Lin, 3Fl., No. 17, Jiang S.St., Neihu Chiu, Taipei 114; Kan-Jung Yang, No. 40, Lane 113, Hangjou Rd., Jungli City, Taoyuan 320, all of (TW)

( * ) Notice: Subject to any disclaimer, the term of this patent is extended or adjusted under 35 U.S.C. 154(b) by 0 days.

(21) Appl. No.: 09/802,938

(22) Filed: Mar. 12, 2001

(51) Int. Cl.[7] .............................................. G08B 21/00
(52) U.S. Cl. ........................ 340/618; 340/623; 73/304; 73/305; 604/254
(58) Field of Search ................................. 340/618, 623, 340/624; 73/304, 305; 604/65, 297, 254, 255; 128/DIG. 13

(56) References Cited

U.S. PATENT DOCUMENTS

| | | | | |
|---|---|---|---|---|
| 4,970,498 A | * | 11/1990 | Hwang | ........................ 340/624 |
| 5,950,487 A | * | 9/1999 | Maresca, Jr. et al. | ......... 73/293 |
| 6,028,521 A | * | 2/2000 | Issachar | ...................... 340/624 |
| 6,195,012 B1 | * | 2/2001 | Yang | ........................... 340/618 |
| 6,218,949 B1 | * | 4/2001 | Issachar | ...................... 340/624 |
| 6,261,267 B1 | * | 7/2001 | Chen | ........................... 604/247 |

* cited by examiner

Primary Examiner—Edward Lefkowitz
(74) Attorney, Agent, or Firm—Dougherty & Troxell

(57) ABSTRACT

An automatic infusion-monitoring instrument includes a clip adapted to clamp a flow-indicating cylinder of an infusion set corresponding to a liquid level in the cylinder that keeps unchanged when there is sufficient amount of infusion liquid in the infusion set, a floater pre-disposed in the flow-indicating cylinder to move upward and downward along with the liquid level in the flow-indicating cylinder, a detecting unit having an emitter and a receiver mounted in the clip to normally face the floater, and an alarm unit electrically connected to the detecting unit via a conducting wire. When the liquid level in the flow-indicating cylinder lowers so that the floater is moved to locate below the emitter and the receiver and no longer blocks the wave emitted by the emitter, the alarm unit is actuated to emit sound, voice, light or flash as a warning signal of running-out infusion liquid.

12 Claims, 6 Drawing Sheets

AUTOMATIC INFUSION-MONITORING INSTRUMENT

BACKGROUND OF THE INVENTION

The present invention relates to an automatic infusion-monitoring instrument, and more particularly to an infusion-monitoring instrument having a detecting unit mounted in a clip that is adapted to clamp on a flow-indicating cylinder of an infusion set for emitter and receiver of the detecting unit to locate at a position corresponding to a floater freely floating on a liquid level in the flow-indicating cylinder, and an alarm unit electrically connected to the detecting unit to emit warning signal when the liquid level and the floater are detected to lower and locate below the emitter and receiver.

An infusion set is frequently used in medical treatments and typically includes an infusion liquid container, a flow-indicating cylinder connected to a lower side of the liquid container, a liquid duct extended from a lower end of the flow-indicating cylinder, a flow regulator mounted on the liquid duct at an adequate position, and an injection needle connected to a free end of the liquid duct. Generally, a liquid level in the flow-indicating cylinder is observed from time to time in order to timely find out whether an infusion liquid is running out, so that the flow regulator could be timely shut off to prevent the patient's blood from undesirably flowing into the injection needle and the liquid duct. Such manual observation of the liquid level in the flow-indicating cylinder from time to time causes considerable inconvenience to the patient, the attendant family and the nurse.

There has been developed different electronic instruments to control the time, dosage and flow of an infusion. However, these electronic instruments normally have big volume and high manufacturing cost, and are usually employed only in infusion for special medical treatments in which time, dosage and flow of infusion need special control. These bulky and expensive instruments for electronically controlling infusion are therefore not widely employed in general infusions for general medical treatments.

There is also developed an automatic infusion-monitoring instrument that includes a sensing element being inserted into the infusion liquid container to direct contact with the infusion liquid. The sensing element is provided with a trigger point that is electrically connected to a sensing circuit and an alarm. This type of automatic infusion-monitoring instrument is very expensive and is not disposable to meet the hygienic requirement. Moreover, the sensing element tends to pierce through an infusion liquid container in the form of a plastic bag.

It is therefore desirable to develop an improved automatic infusion-monitoring instrument to eliminate the above-mentioned drawbacks.

SUMMARY OF THE INVENTION

A primary object of the present invention is to provide an automatic infusion-monitoring instrument that enables electronic monitoring of infusion liquid level in the flow-indicating cylinder to timely emit a signal to an attendant or nurse as a warning of an empty infusion liquid container.

Another object of the present invention is to provide an automatic infusion-monitoring instrument that has simple structure to meet the economical principle and the hygienic requirement.

To achieve the above and other objects, the automatic infusion-monitoring instrument of the present invention mainly includes a clip adapted to clamp a flow-indicating cylinder of an infusion set corresponding to a liquid level in the cylinder that keeps unchanged when there is sufficient amount of infusion liquid in the infusion set, a floater pre-disposed in the flow-indicating cylinder to move upward and downward along with the liquid level in the flow-indicating cylinder, a detecting unit having an emitter and a receiver mounted in the clip to normally face the floater, and an alarm unit electrically connected to the detecting unit via a conducting wire. When the liquid level in the flow-indicating cylinder lowers so that the floater is moved to locate below the emitter and the receiver and no longer blocks wave emitted from the emitter, the alarm unit is actuated to emit sound, voice, light or flash as a warning signal of running-out infusion liquid.

The clip can be easily operated and repeatedly used while the floater is disposable, allowing the automatic infusion-monitoring instrument of the present invention to be economical and practical for use.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein

FIG. 6 shows a run-out infusion liquid is detected through the projection-type detection by the detecting unit of the present invention and the alarm unit thereof is on;

FIG. 10 shows a run-out infusion liquid is detected through the reflection-type detection by the detecting unit of the present invention and the alarm unit thereof is on.

DETAILED DESCRIPTION OF THE PREFERRED EMBODIMENTS

Figure 1:
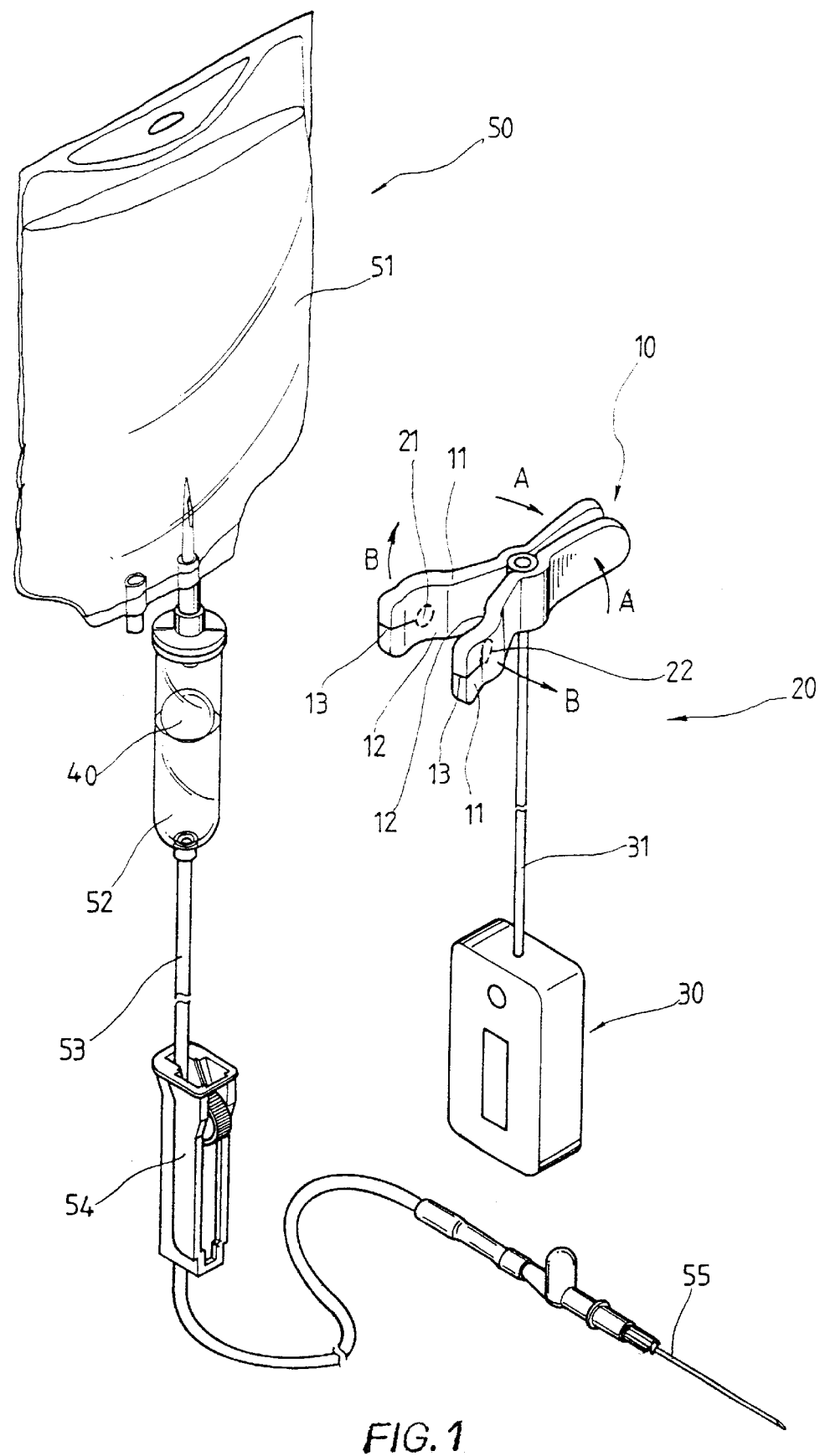
FIG. 1 is a perspective showing an automatic infusion-monitoring instrument according to an embodiment of the present invention.
Figure 2:
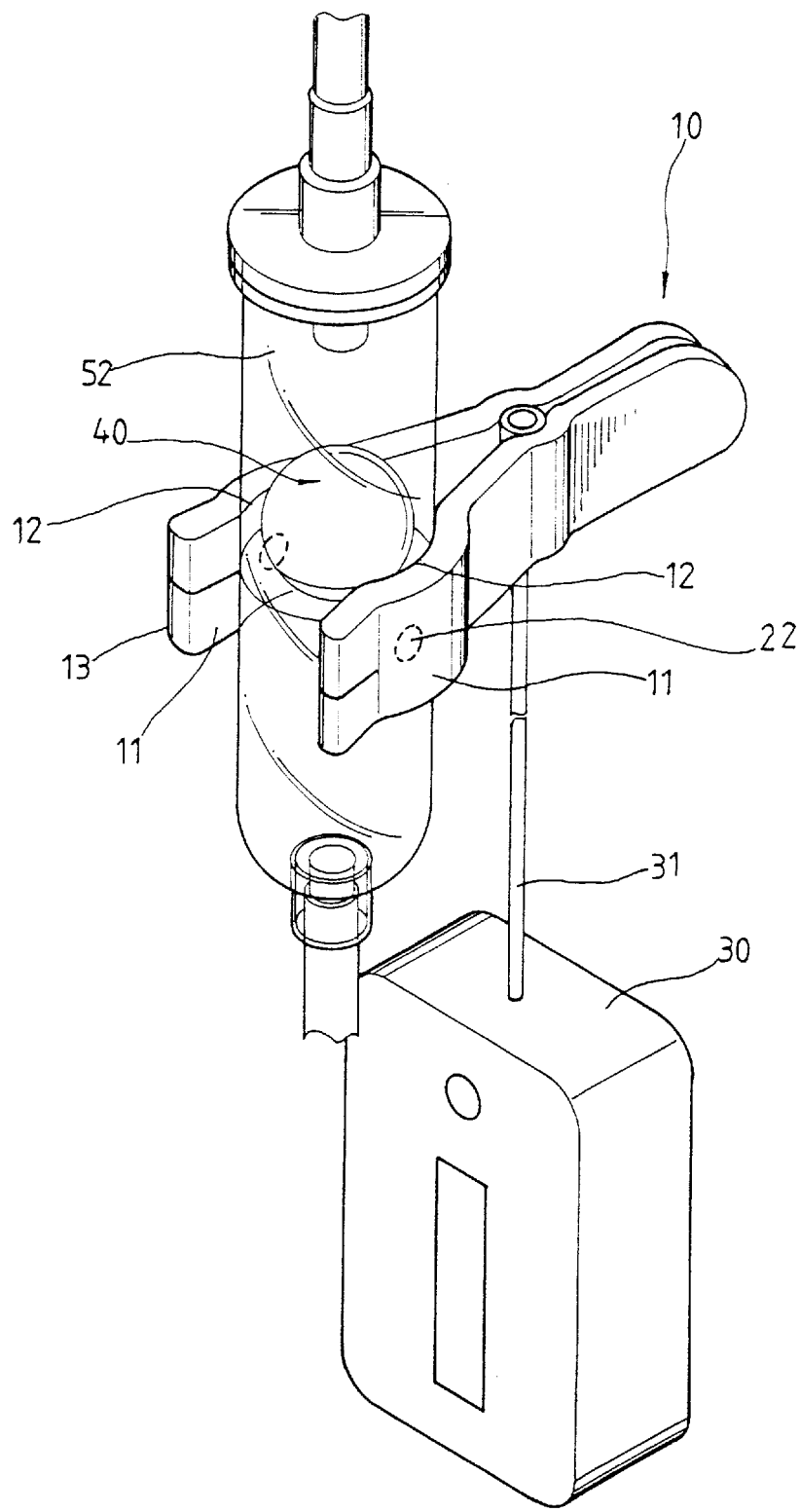
FIG. 2 shows a clip of the automatic infusion-monitoring instrument of FIG. 1 holds a flow-indicating cylinder between two claws of the clip.
Figure 3:
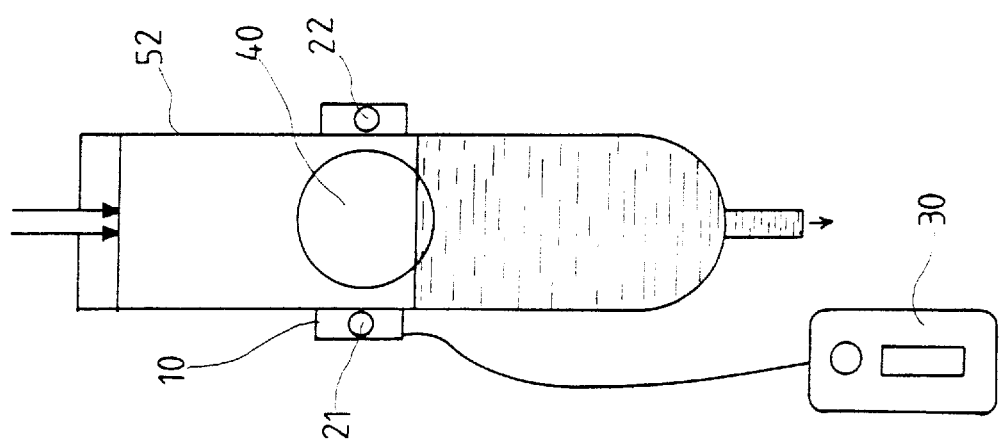
FIG. 3 is a schematical view showing the operation of the infusion-monitoring instrument of FIG. 1.

Please refer to FIGS. 1, 2 and 3 in which an automatic infusion-monitoring instrument according to the present invention is shown. The automatic infusion-monitoring instrument mainly includes a clip 10 having two claws 11, a detecting unit 20 including an emitter 21 and a receiver 22 mounted on the clip 10, an alarm unit 30 electrically connected to the detecting unit 20, and a floater 40 disposed in a flow-indicating cylinder 52 of an infusion set 50. To use the automatic infusion-monitoring instrument of the present invention, the clip 10 is brought to firmly clamp a flow-indicating cylinder 52 of the infusion set 50 between the two claws 11.

An infusion set 50 typically includes an infusion liquid container 51, a flow-indicating cylinder 52 connected to a lower side of the liquid container 51, a liquid duct 53 extended from a lower end of the flow-indicating cylinder 52, a flow regulator 54 mounted on the liquid duct 53 at an adequate position, and an injection needle 55 connected to a free end of the liquid duct 53. Among the elements of the infusion set 50, only the liquid container 51 and the flow-indicating cylinder 52 can effectively reflect a level of liquid in the liquid container 51. The liquid container 51 may be a rigid glass bottle that usually has a large diameter or a soft plastic bag that usually has an insufficient rigidity and tends to change its shape with reduction of liquid therein. Thus, the liquid container 51, either in the form of a glass bottle or a plastic bag, is not suitable for direct association with the automatic infusion-monitoring instrument of the present invention by clamping two claws 11 of the clip 10 on the liquid container 51. On the other hand, the flow-indicating cylinder 52 usually has an outer diameter about 1.5 cm and a height about 5 cm, and has a sufficient rigidity. When the flow-indicating cylinder 52 is selected as a monitoring target, the clip 10 is brought to hold the cylinder 52 at an outer surface of the cylinder 52 without contacting with the infusion liquid at all. Therefore, the clip 10 may be repeatedly used and the use of it to hold the flow-indicating cylinder 52 completely meets hygienic requirements.

There are various structural designs available for clip 10. However, it is preferable the clip 10 is made into a regular size of the flow-indicating cylinder 52, so that the clip 10 can be mass-produced to lower its manufacturing cost and be conveniently operated for repeated use. For example, the clip 10 may be designed into a spring clip with suitable dimensions, as shown in FIGS. 1 and 2, and the two claws 11 thereof are provided near their front ends with two curved clamping portions 12 to facilitate fitly contact of the claws 11 with the round-sectioned flow-indicating cylinder 52. Whereby, the clip 10 could be brought to firmly hold the flow-indicating cylinder 52 at a predetermined height simply by pressing two rear portions of the clip 10 toward each other, as indicated by arrows A in FIG. 1, so as to open the two claws 11, as indicated by arrows B in FIG. 1. The claws 11 are optionally provided at outer surfaces with marks 13 to indicate exact positions of the emitter 21 and the receiver 22 mounted in the clip 10, and thereby enables easy locating of the clip 10 on the flow-indicating cylinder 52 at a desired position. It is also preferable that the liquid level in the flow-indicating cylinder 52 could still be visually checked after the cylinder 52 has been clamped between the claws 11 of the clip 10.

The emitter 21 and the receiver 22 of the detecting unit 20 are mounted in the claws 11 of the clip 10 at predetermined positions that would be further described later. The emitter 21 and the receiver 22 are designed to emit and receive, respectively, infrared light, magnetic wave or laser to perform a detecting function. In a first embodiment of the present invention, the emitter 21 and the receiver 22 are separately mounted on the two claws 11 in the curved clamping portions 12 at the same level to face each other, so that the receiver 22 only receives infrared light, magnetic wave or laser that is emitted by the emitter 21 and directly projected onto the receiver 22, as shown in FIGS. 3 through 7. Detecting of infusion liquid level in the flow-indicating cylinder 52 through this type of arrangement of the emitter 21 and the receiver 22 is referred to herein as the "projection-type detection." And, in a second embodiment of the present invention, the emitter 21 and the receiver 22 are mounted on the same one claw 11 in the curved clamping portion 12 to face toward the same direction, so that the receiver 22 only receives infrared light, magnetic wave or laser that is emitted by the emitter 21 and reflected from the floater 40 onto the receiver 22, as shown in FIGS. 8 through 11. Detecting of infusion liquid level in the flow-indicating cylinder 52 through this second type of arrangement of the emitter 21 and the receiver 22 is referred to herein as the "reflection-type detection."

The floater 40 is an opaque member being pre-disposed in the flow-indicating cylinder 52 and is designed as a disposable product to be discarded along with the infusion set 50 after the same has been used. The floater 40 may be of any shape, such as a ball, an oblong body, a tube, etc., and has dimensions allowing it to freely float on the infusion liquid level in the flow-indicating cylinder 52. When there is sufficient infusion liquid in the container 51 of the infusion set 50, the infusion liquid level, and accordingly, the position of the floater 40, in the cylinder 52 keeps unchanged. This unchanged position of the floater 40 is referred to hereinafter as the "normal position". When the infusion liquid in the container 51 gradually decreases to an amount not sufficient to keep the infusion liquid level in the cylinder 52, the liquid level lowers and brings the floater 40 to descend in the cylinder 52. This lowered position of the floater 40 is referred to hereinafter as the "lowered position". Thus, it is preferable the two claws 11 of the clip 10 clamp the cylinder 52 at the normal position. That is, it is preferable to position the emitter 21 and the receiver 22 of the detecting unit 20 corresponding to the normal position.

The alarm unit 30 is electrically connected to the detecting unit 20 via a conducting wire 31. A length of the conducting wire 31 is determined depending on actual needs. The alarm unit 30 may be in the form of a buzzer, a horn for emitting musical sound or voice, or a light-emitting device for lighting or flashing. Alternatively, additional infrared (IR) or radio-frequency (RF) transmission system may be used to transmit warning messages from the alarm unit 30 to other alarms or a nursing care station at a remote location to achieve the best monitoring function. Since internal wirings for the alarm unit 30 and the detecting unit 20 can be designed through currently available electronic technologies, they are not particularly described herein.

The operation of the automatic infusion-monitoring instrument according to the present invention will now be described in more details as below.

Figure 5:
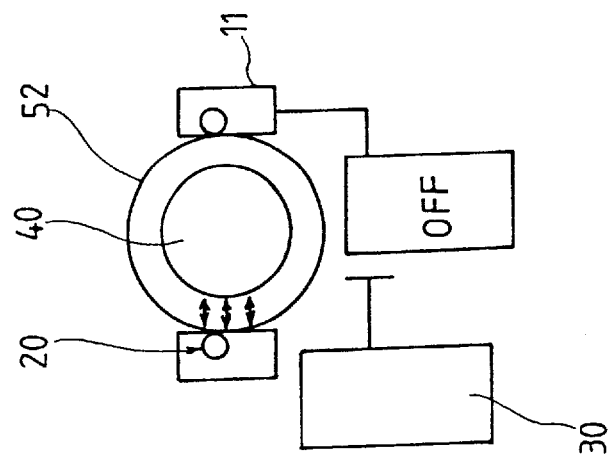
FIG. 5 is a top view of FIG. 4.
Figure 4:
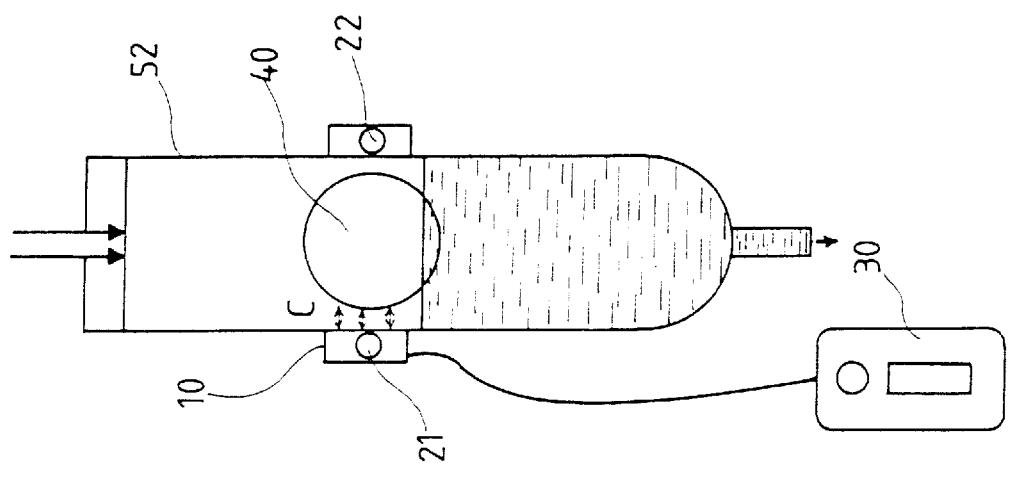
FIG. 4 shows a sufficient amount of infusion liquid is detected through a projection-type detection by a detecting unit of the present invention and an alarm unit thereof is off.
Figure 6:
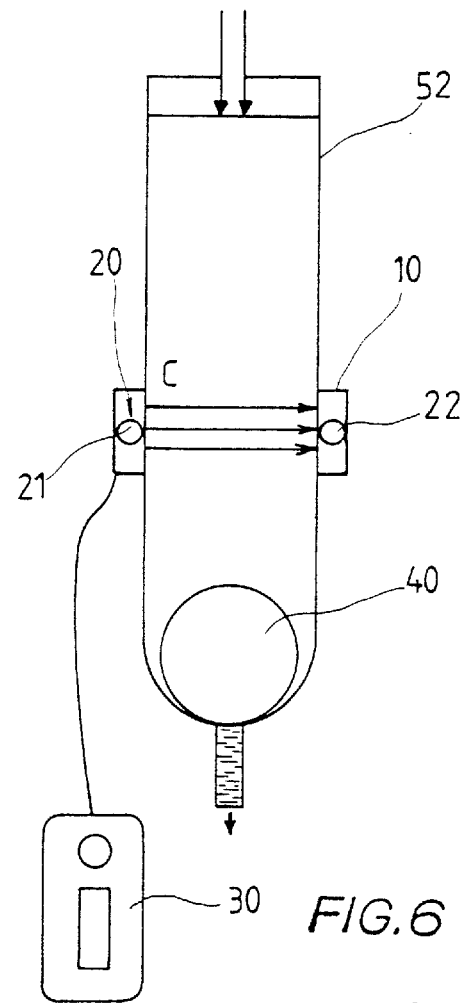
Figure 7:
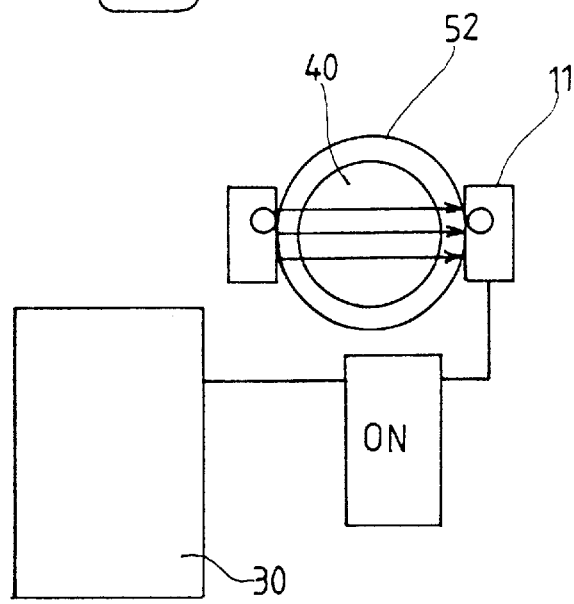
FIG. 7 is a top view of FIG. 6.

In the case of the first embodiment of the present invention in which the "projection-type detection" is performed, the emitter 21 and the receiver 22 are separately located at two diametrically opposite sides of the flow-indicating cylinder 52 corresponding to the "normal position", as shown in FIG. 3. When the infusion liquid container 51 has sufficient amount of infusion liquid contained therein, the floater 40 constantly stays in the cylinder 52 at the normal position between the emitter 21 and the receiver 22. At this point, wave C, such as infrared light, emitted from the emitter 21 is blocked by the opaque floater 40 and the receiver 22 does not receive any signal, as shown in FIGS. 4 and 5. At this point, a circuit between the detecting unit 20 and the alarm unit 30 is broken and the alarm unit 30 is not actuated. When the infusion liquid in the container 51 runs out and the liquid level in the flow-indicating cylinder 52 gradually lowers, the floater 40 on the infusion liquid also descends with the lowered liquid level to finally locate below the emitter 21 and the receiver 22. At this point, wave C emitted from the emitter 21 is not blocked by the floater 40 and is directly projected onto the receiver 22, permitting the receiver 22 to receive a signal. At this point, the circuit between the detecting unit 20 and the alarm unit 30 is closed and the alarm unit 30 is actuated, as shown in FIGS. 6 and 7.

Figure 8:
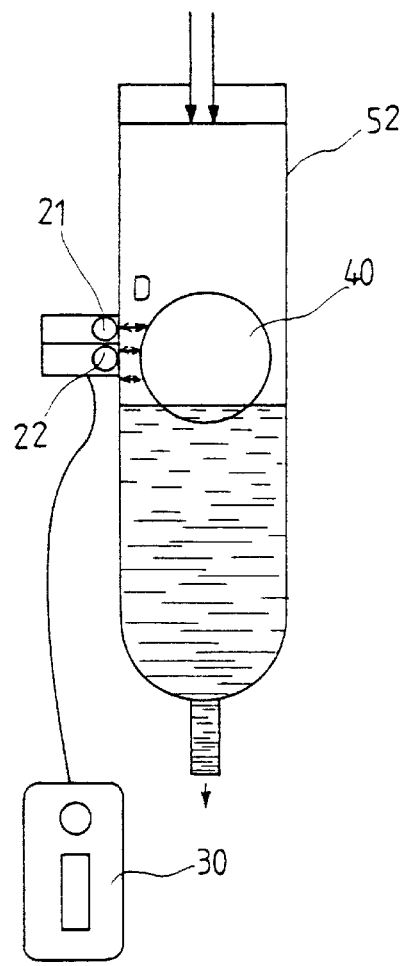
FIG. 8 shows a sufficient amount of infusion liquid is detected through a reflection-type detection by the detecting unit of the present invention and the alarm unit thereof is off.
Figure 9:
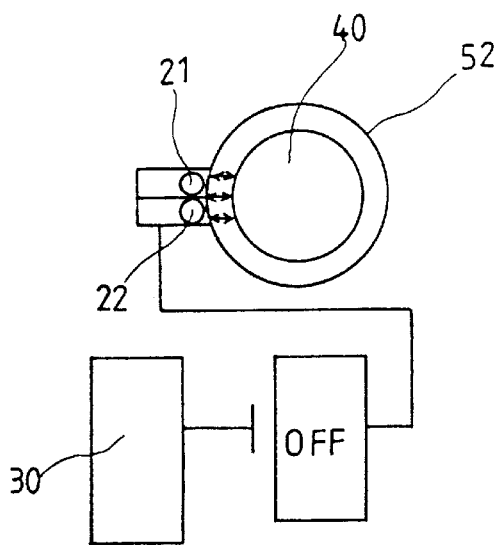
FIG. 9 is a top view of FIG. 8.
Figure 10:
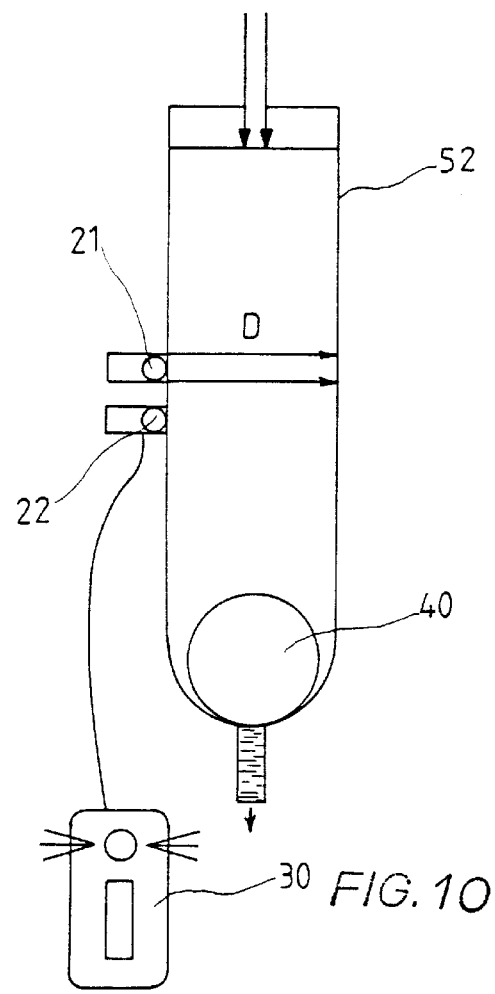
Figure 11:
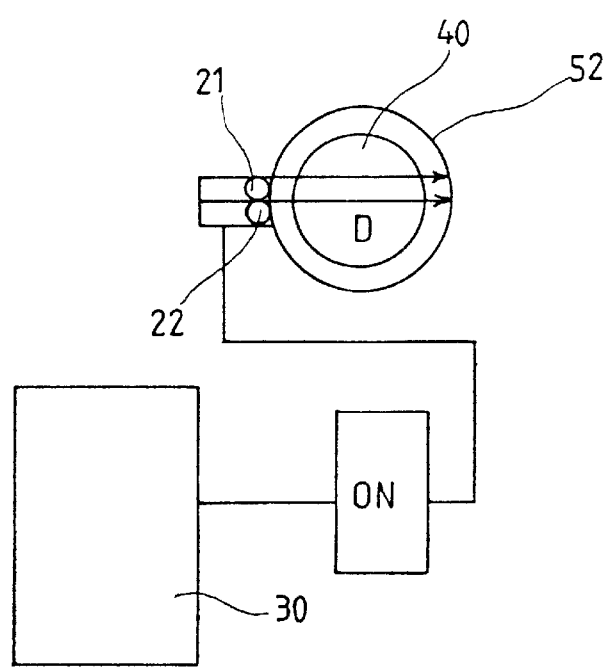
FIG. 11 is a top view of FIG. 10.

And, in the case of the second embodiment of the present invention in which the "reflection-type detection" is performed, the emitter 21 and the receiver 22 are located at the same side of the flow-indicating cylinder 52 corresponding to the "normal position", as shown in FIG. 8. When the infusion liquid container 51 has sufficient amount of infusion liquid contained therein, the floater 40 constantly stays in the cylinder 52 at the normal position in front of the emitter 21 and the receiver 22. At this point, wave D, such as infrared light, emitted from the emitter 21 is blocked by the floater 40 and reflected from the floater 40 onto the receiver 22, so that the receiver 22 receives a signal from the reflected wave D, as shown in FIGS. 8 and 9. At this point, a circuit between the detecting unit 20 and the alarm unit 30 is broken and the alarm unit 30 is not actuated. When the infusion liquid in the container 51 runs out and the liquid level in the flow-indicating cylinder 52 gradually lowers, the floater 40 on the infusion liquid also descends with the lowered liquid level to finally locate below the emitter 21 and the receiver 22. At this point, wave D emitted from the emitter 21 is not blocked by the floater 40 and is projected forward without being received by the receiver 22. That is, the receiver 22 does not receive any signal. At this point, the circuit between the detecting unit 20 and the alarm unit 30 is closed and the alarm unit 30 is actuated, as shown in FIGS. 10 and 11.

With the above arrangements, the automatic infusion-monitoring instrument of the present invention is structurally simple but novel and could effectively achieve the purpose of detecting a running-out infusion liquid and timely warning related persons of such condition. The present invention is therefore novel and practical for use.

What is claimed is:

1. An automatic infusion-monitoring instrument, comprising a clip having two claws, a detecting unit including an emitter and a receiver mounted on said clip, an alarm unit electrically connected to said detecting unit, and a floater;

said clip being adapted to firmly clamp a rigid flow-indicating cylinder of an infusion set between said two claws without deforming said flow-indicating cylinder; and said claws being provided at inner surfaces facing each other with curved portions for said claws to fitly contact with an outer surface of said flow-indicating cylinder which has a round cross section;

said emitter and said receiver of said detecting unit being mounted in said claws of said clip at predetermined positions; and said emitter being able to emit wave and said receiver being able to receive said wave emitted by said emitter as a signal to control an actuation of said alarm unit;

said alarm unit being electrically connected to said detecting unit via a conducting wire to receive a signal from said detecting unit; and said floater being an opaque member pre-disposed in said flow-indicating cylinder, and having dimensions permitting said floater to freely float on an infusion liquid in said flow-indicating cylinder and descend along with a lowered liquid level in said flow-indicating cylinder; whereby when there is sufficient amount of infusion liquid in said infusion set, said floater constantly stays in said flow-indicating cylinder at a normal position corresponding to said emitter and said receiver of said detecting unit, and when said infusion liquid in said infusion set runs out and said liquid level in said flow-indicating cylinder lowers, said floater descends to locate below said emitter and said receiver.

2. The automatic infusion-monitoring instrument as claimed in claim 1, wherein said emitter and said receiver are separately mounted in said two claws of said clip to locate at two diametrically opposite sides of said flow-indicating cylinder when the latter is clamped between said two claws, and wherein when said wave emitted from said emitter is blocked by said floater located at said normal position, and said receiver does not receive said wave emitted from said emitter as a signal, a circuit between said detecting unit and said alarm unit is broken and said alarm unit is not actuated, and when said wave emitted from said emitter is not blocked by said floater located below said normal position, and said receiver receives said emitted wave as a signal, the circuit between said detecting unit and said alarm unit is closed and said alarm unit is actuated to emit a warning signal.

3. The automatic infusion-monitoring instrument as claimed in claim 1, wherein said emitter and said receiver are mounted in one of said two claws of said clip to locate at the same side of said flow-indicating cylinder when the latter is clamped between said two claws, and wherein when said wave emitted from said emitter is blocked by and reflected from said floater located at said normal position and said receiver receives said emitted and reflected wave as a signal, a circuit between said detecting unit and said alarm unit is broken and said alarm unit is not actuated, and when said wave emitted from said emitter is not blocked by said floater located below said normal position, and said receiver does not receive any said emitted wave as a signal, the circuit between said detecting unit and said alarm unit is closed and said alarm unit is actuated to emit a warning signal.

4. The automatic infusion-monitoring instrument as claimed in claim 1, wherein said clip is made into a regular size of said flow-indicating cylinder, so that said clip can be conveniently operated to firmly clamp said flow-indicating cylinder.

5. The automatic infusion-monitoring instrument as claimed in claim 1, wherein said flow-indicating cylinder has clear area exposed to outside after said clip has been clamped onto said flow-indicating cylinder, so that a liquid level in said flow-indicating cylinder can still be visually checked.

6. The automatic infusion-monitoring instrument as claimed in claim 1, wherein said wave emitted by said emitter is infrared light.

7. The automatic infusion-monitoring instrument as claimed in claim 1, wherein said wave emitted by said emitter is magnetic wave.

8. The automatic infusion-monitoring instrument as claimed in claim 1, wherein said wave emitted by said emitter is laser.

9. The automatic infusion-monitoring instrument as claimed in claim 1, wherein said alarm unit is a buzzer.

10. The automatic infusion-monitoring instrument as claimed in claim 1, wherein said alarm unit is a horn.

11. The automatic infusion-monitoring instrument as claimed in claim 1, wherein said alarm unit is a light emitting device.

12. The automatic infusion-monitoring instrument as claimed in claim 1, wherein said alarm unit is adapted to transmit a warning signal to other alarms at remote locations via additional infrared (IR) or radio-frequency (RF) transmission systems.

* * * * *